United States Patent [19]

Sherman

[11] 4,388,831
[45] Jun. 21, 1983

[54] ULTRASONIC PROBE FOR NONDESTRUCTIVE INSPECTION

[75] Inventor: Ira N. Sherman, Cincinnati, Ohio

[73] Assignee: General Electric Company, Cincinnati, Ohio

[21] Appl. No.: 236,086

[22] Filed: Feb. 20, 1981

[51] Int. Cl.³ .......................................... G01N 29/04
[52] U.S. Cl. ........................................ 73/623; 73/632
[58] Field of Search ............... 73/623, 632, 633, 661, 73/638

[56] References Cited

U.S. PATENT DOCUMENTS

| | | | |
|---|---|---|---|
| 2,995,925 | 8/1961 | Worlton | 73/67.7 |
| 3,028,752 | 4/1962 | Bacon | 73/67.8 |
| 3,417,609 | 12/1968 | Graham | 73/71.5 |
| 3,583,211 | 6/1971 | Brech | 73/623 |
| 3,584,504 | 6/1971 | Proctor et al. | 73/67.8 |
| 3,608,363 | 9/1971 | Whittington | 73/623 |
| 3,636,778 | 1/1972 | Huffstetler | 73/67.8 R |
| 3,898,838 | 8/1975 | Connelly | 73/67.8 S |
| 3,969,926 | 7/1976 | Walker et al. | 73/67.8 S |
| 3,978,714 | 9/1976 | Shraiber et al. | 73/67.8 S |
| 4,037,465 | 7/1977 | Cook et al. | 73/67.8 S |
| 4,102,206 | 7/1978 | Perdijon | 73/644 |
| 4,177,679 | 12/1979 | Soldner | 73/633 |

Primary Examiner—Anthony V. Ciarlante
Attorney, Agent, or Firm—Gregory A. Welte; Carl L. Silverman; Derek P. Lawrence

[57] ABSTRACT

A probe is disclosed for the nondestructive inspection of the interior walls of cylindrical recesses, comprising an elongated shaft having an ultrasonic transducer mounted thereon a predetermined distance from the longitudinal axis of the shaft and oriented for directing the axis of radiation of ultrasonic energy emanating from the transducer outwardly in a plane perpendicular to the longitudinal axis of the shaft. In another embodiment, the probe comprises a shaft having a lateral extension whereon a first ultrasonic transducer is mounted at a predetermined distance from the longitudinal axis of the shaft and is oriented for directing the axis of radiation of ultrasonic energy emanating therefrom parallel to a line formed by the intersection of planes perpendicular to the longitudinal axes of the shaft and lateral extension. A second ultrasonic transducer is mounted on the longitudinal axis of the shaft and is oriented for radially outward direction of the axis of radiation of ultrasonic energy emanating therefrom. The second ultrasonic transducer is effective for centering the probe within the hole under inspection. The predetermined distance of the first ultrasonic transducer relative to the longitudinal axis of the shaft determines the angle of refraction of the radiated ultrasonic energy and can be predetermined in accordance with the desired inspection mode.

4 Claims, 6 Drawing Figures

U.S. Patent      Jun. 21, 1983      4,388,831
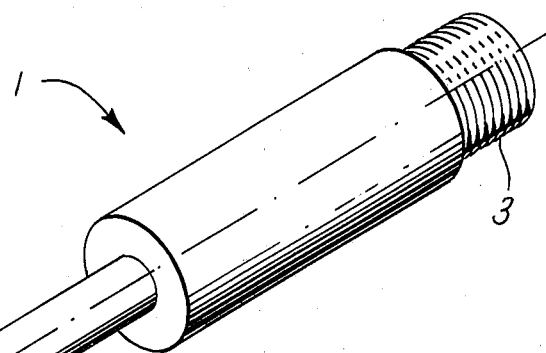
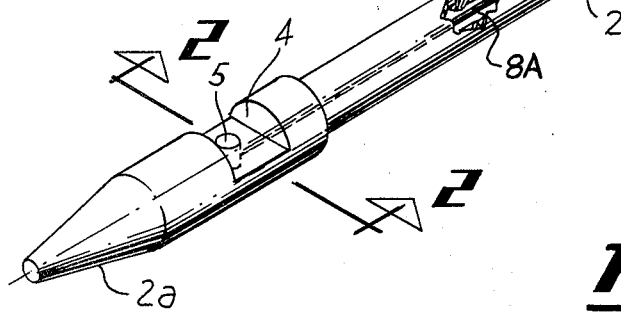
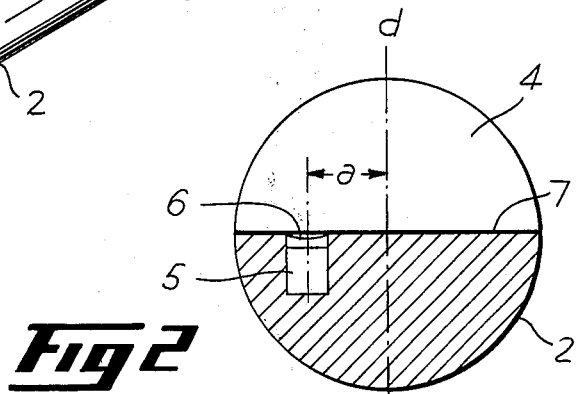
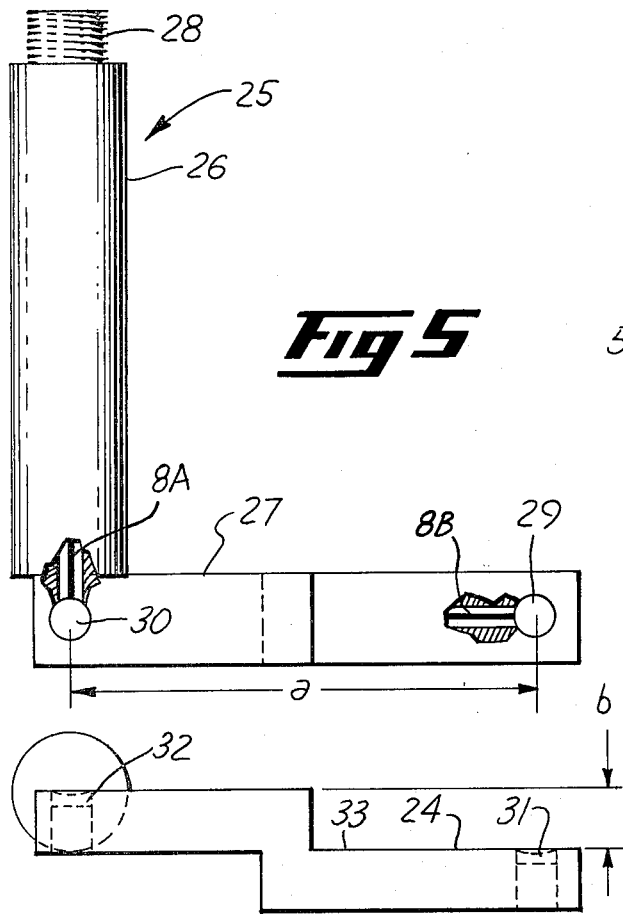
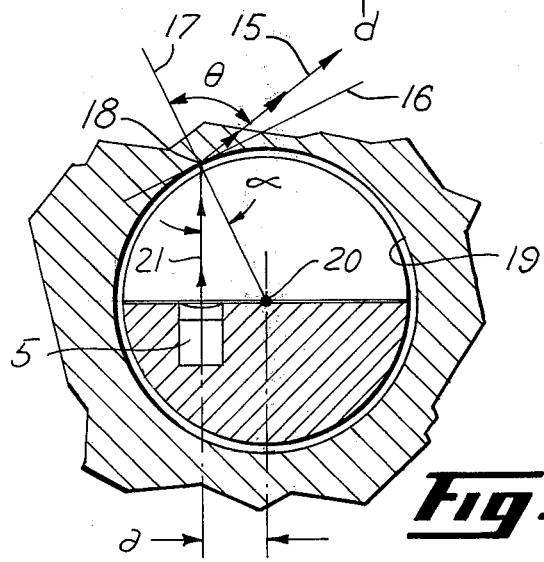
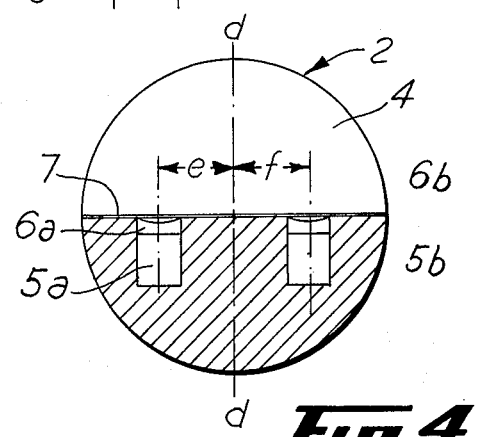

ULTRASONIC PROBE FOR NONDESTRUCTIVE INSPECTION

BACKGROUND OF THE INVENTION

The present invention relates to apparatus for nondestructive testing and inspecting of objects. More specifically, it relates to a new and improved probe which is effective for detecting anomalies on and beneath the surface of an object having recesses, e.g., cylindrical, egg-shaped, and other conventional recess configurations, by subjecting the interior surface of the recess to ultrasonic energy.

The use of nondestructive inspection means, such as X-rays or ultrasonic energy, for the detection of anomalies on and/or beneath the surfaces of objects is well known. However, present techniques are not fully satisfactory in connection with the circumferential inspection of bolt or bore holes, especially relatively small diameter holes.

The desired application of such inspection means also requires that the inspection means be compatible with computer control in a production environment and be capable of a high degree of reproducibility of results.

SUMMARY OF THE INVENTION

An object of the present invention is to provide a new and improved probe effective for detecting anomalies on and/or beneath the surface of an object.

Another object of the present invention is to provide a probe effective for detecting such anomalies on an object having cylindrical recesses, such as bolt or bore holes, formed therein.

Another object of the present invention is to provide a probe effective for detecting such anomalies on an object having cylindrical recesses by subjecting the surface of the object to ultrasonic energy.

Another object of the present invention is to provide a probe effective for detecting such anomalies on an object having cylindrical recesses with the probe being of a type adaptable for various inspection modes of operation.

Another object of the present invention is to provide a probe effective for detecting such anomalies on an object having cylindrical recesses, which probe can be rotated and translated axially in order to circumferentially inspect for anomalies along the entire inside surface of the recesses and which probe is adapted for computer controlled inspection.

Still another object of the present invention is to provide a probe effective for detecting such anomalies on an object having cylindrical recesses therein, which probe is efficient and economically employable for the repetitive inspection of such recesses with a high degree of reproducibility of results.

In accordance with one embodiment of the present invention, the probe comprises an elongated shaft, a predeterminedly oriented ultrasonic transducer affixed to the shaft and displaced a predetermined distance from the longitudinal axis thereof. The probe is adapted to be rotated and translated axially in a cylindrical recess in an object for inspecting for anomalies on and/or beneath the surface of the object.

In another embodiment, the probe comprises an elongated shaft having a lateral extension whereon an ultrasonic transducer is mounted and displaced a predetermined distance from the longitudinal axis of the shaft.

BRIEF DESCRIPTION OF THE DRAWINGS

FIG. 1 is a perspective illustration of one embodiment of the ultrasonic probe of the present invention.

FIG. 2 is a partial sectional view taken along line 2—2 of FIG. 1.

FIG. 3 is a diagram illustrating a manner of determining a desired inspection mode angle for use with the probe of FIGS. 1 and 2.

FIG. 4 is a partial sectional view, taken as in FIG. 2, illustrating a modification of the embodiment of the present invention shown in FIG. 1.

FIG. 5 is an elevational view of a second embodiment of the ultrasonic probe of the present invention.

FIG. 6 is a simplified bottom plan view of the probe shown in FIG. 5.

DETAILED DESCRIPTION OF THE INVENTION

Referring to FIG. 1, an embodiment of an ultrasonic probe 1 of the present invention is shown. The probe 1 comprises an elongated shaft 2, an electrical connector 3 mounted on an end of the shaft, a lateral recess 4 formed in the shaft and a conventional ultrasonic transducer 5 mounted on the shaft in the bottom of the recess. The probe 1 is effective for circumferential nondestructive inspection for anomalies on and/or beneath the interior surface, i.e., in the subsurface, of a cylindrical recess in an object by subjecting the involved surface to ultrasonic energy. Preferably, the other end 2a of the probe is tapered to facilitate entry of the probe into the recess under inspection.

Referring to FIG. 2, the lateral recess 4 is preferably a lateral cutout having a planar bottom surface 7 preferably parallel with but not necessarily coplanar with the longitudinal axis of the shaft 2. Additionally, the depth of the lateral cutout is not critical to the present invention. The ultrasonic transducer 5 is preferably mounted in the bottom of the lateral recess at a predetermined distance or offset "a" from a central axis d-d of the shaft 2. The predetermined distance "a" is measured between the axis of radiation of ultrasonic energy emanating from the transducer and the longitudinal axis of the shaft along a line which is perpendicular to both the axes.

It is to be appreciated that a lateral recess or cutout is not essential in that the ultrasonic transducer 5 can be supported by the shaft or mounted in the side thereof. However, having the transducer 5 in the cutout is preferable in that it affords protection to the transducer. Regardless of where the ultrasonic transducer 5 is mounted or supported, it is oriented for directing the axis of radiation of the ultrasonic energy emanating from the transducer outwardly in a plane perpendicular to the longitudinal axis of the shaft 2. A conventional lens 6 is provided to protect the ultrasonic transducer and to seal the recess in which the ultrasonic transducer is mounted.

As will be discussed more fully later, a second ultrasonic transducer (not shown in FIG. 2) can be supported or mounted in the same manner as the first ultrasonic transducer 5. This second transducer is oriented for radially outward direction of the axis of radiation of ultrasonic energy emanating therefrom and is effective for centering the probe within the hole under inspection using the inspection method described hereinafter.

The predetermined distance of offset "a" is calculated using the following expression:

$$a = \left(\frac{D}{2}\right) \times \left(\frac{V1}{V2}\right) \times \sin\theta \quad (1)$$

wherein: "a" is the predetermined distance; "D" is the diameter of the hole in the object to be inspected; "V1" is the longitudinal velocity of sound in water; "V2" is the inspection mode velocity in the object to be inspected; "$\theta$" is the desired angle of refraction or desired inspection mode angle.

The determination of the desired angle of refraction or desired inspection mode angle "$\theta$" is shown diagrammatically in FIG. 3. The axis of ultrasonic radiation 21 strikes the interior wall 19 of a hole being inspected at a point 18. A tangent 16 is drawn through the point of intercept 18. A normal 17 to the tangent is drawn through the point of intercept 18 and the center 20 of the hole under inspection. The angle "$\theta$" is measured between the normal 17 and the axis of the refracted ultrasonic energy 15.

The inspection mode velocity in the object to be inspected "V2" is a function of the type of material under inspection and may be obtained from the Standard Handbook for Mechanical Engineers, 7th edition, McGraw-Hill Book Company, 1967, p. 12–177, and the references cited therein.

Referring to FIGS. 2 and 3, the distance "a" by which the ultrasonic transducer 5 is offset from the central axis d-d of the shaft 2 determines the angle of incidence "$\alpha$" of the axis of radiation of the ultrasonic energy on the surface of the hole wall 19 under inspection for a given diameter hole. Therefore, the offset "a" determines the desired angle of refraction or the desired inspection mode angle "$\theta$" for a given diameter hole. As is well known in the art, the desired angle of refraction "$\theta$" determines the acoustic inspection mode, namely, shear wave, longitudinal wave or surface wave mode, for which a given probe is effective for inspection use. Thus, for a given diameter hole, a plurality of probes having different values of offset "a" can be manufactured prior to inspection and the probe which produces the appropriate angle of refraction for the desired inspection mode can be selected at the time of inspection.

In preparation for the ultrasonic circumferential inspection of the interior walls of cylindrical bolt or bore holes for anomalies on and/or beneath the surface of an object, and which may conceivably constitute flaws in the object, the hole to be inspected is filled with an ultrasonic coupling medium such as water. The elongated shaft 2 is inserted into the hole under inspection such that the axis of radiation of the ultrasonic transducer 5 intercepts the wall of the hole under inspection. During inspection the probe is rotated and after each complete revolution, the probe is translated axially a pre-set distance along the longitudinal axis of the hole.

The outside diameter of the elongated shaft 2 is preferably manufactured slightly smaller than the inside diameter of the hole to be inspected. The smaller diameter for the shaft helps prevent it from binding in the hole during rotation and translation of the probe during inspection. The slightly smaller diameter of the shaft also centralizes the probe in the hole without the use of any additional centering means or method, which serves to maintain the proper angle of incidence of the axis of radiation of the transmitted ultrasonic energy onto the surface of the hole wall under inspection and thus tends to maintain the desired angle of refraction "$\theta$". Preferably, the diameter of the shaft 2 is no more than about 0.005 inches less than the diameter of the hole under inspection.

After the elongated shaft 2 has been inserted into the hole under inspection which has been filled with water, the ultrasonic transducer 5 is electrically stimulated to produce pulses of ultrasonic energy, which pulses are directed at the interior surface of the hole to be inspected for surface and subsurface anomalies. At each discontinuity or anomaly, such as a fissure or void, and at each material interface, a portion of the incident ultrasonic energy is reflected back to the ultrasonic transducer 5 which converts the reflected energy received to electrical impulses. Pattern recognition known in the art is established for the received electrical impulses to evaluate for the possible existence of anomalies.

Although the probe 1, as hereinabove described, is not limited in size with respect to the maximum diameter of the hole it is capable of inspecting, it is particularly effective for inspecting holes with diameters up to about 1.5 inches.

An internal longitudinal passage (partially shown) runs the length of the shaft from the ultrasonic transducer to the electrical connector 3 and at least one electrical lead from the ultrasonic transducer to the electrical connector is run within the passage. Only one lead is needed for each transducer if the shaft is of an electrically conductive material and is used as a common electrical ground reference.

Referring now to FIG. 4, a modification of the hereinabove described embodiment of the present invention, wherein the shaft 2 includes two ultrasonic transducers 5a and 5b mounted in the bottom of recess 4, is partially shown. The lateral recess 4 is preferably a lateral cutout having a planar bottom surface 7, preferably parallel with but not necessarily coplanar with the longitudinal axis of the shaft 2. Additionally, the depth of the lateral cutout 4 is not critical to the present invention. The ultrasonic transducers 5a and 5b are preferably mounted in the bottom of the lateral recess 4 at a predetermined distance or offset "e" and "f", respectively, from a central axis d-d of the shaft 2. The predetermined distances "e" and "f" are measured between the axes of radiation of ultrasonic energy emanating from transducers 5a and 5b, respectively, and the longitudinal axis of the shaft along a line which is perpendicular to the longitudinal axis of the shaft and the respective axis of radiation of ultrasonic energy.

As discussed previously in connection with FIG. 2, a lateral recess or cutout is not essential in the form of invention shown in FIG. 4 in that the ultrasonic transducers can be supported by the shaft or mounted in the side thereof. Regardless of where the ultrasonic transducers 5a and 5b are mounted or supported, they are oriented for directing their axes of radiation of the ultrasonic energy emanating from the transducers outwardly in a plane perpendicular to the longitudinal axis of the shaft 2. Preferably, the axes of radiation of ultrasonic energy emanating from the transducers are parallel and the directions of radiation of ultrasonic energy therefrom are the same. Conventional lenses 6a and 6b are provided to protect the ultrasonic transducers 5a and 5b, respectively, and to seal the recess in which the ultrasonic transducers are mounted.

The predetermined distances or offsets "e" and "f" are calculated according to equation (1) hereinabove described for the predetermined distance "a" of the ultrasonic transducer 5, with the offsets "e" or "f" for the ultrasonic transducers 5a and 5b, respectively, substituted in the equation for "a".

Referring now to the operation of the form of invention shown in FIG. 4, during inspection of the interior walls of a hole, only the first ultrasonic transducer 5a is electrically stimulated to produce pulses of ultrasonic energy. The hole is inspected as is hereinabove described. After the probe has been translated the length of the hole to be inspected, the direction of translation of the probe is reversed and only the second ultrasonic transducer 5b is electrically stimulated to produce pulses of ultrasonic energy. Thus, the second ultrasonic transducer is used to inspect the same interior surface of the hole as the first ultrasonic transducer. However, due to the different direction of offset of the ultrasonic transducers 5a and 5b from the central axis d-d of the probe, the transmitted ultrasonic radiation from each transducer will strike a given point in an object from a different direction. The acoustical properties of certain anomalies create different reflected ultrasonic energy patterns as a function of the angle of ultrasonic inspection. Accordingly, the use of two ultrasonic transducers 5a and 5b in a single probe presents an effective and efficient means for this dual inspection technique.

As shown in FIG. 5, another embodiment of an ultrasonic probe 25 of the present invention comprises a shaft 26 having a lateral extension 27, an electrical connector 28, a first ultrasonic transducer 29 mounted in the lateral extension and a second ultrasonic transducer 30 mounted on the longitudinal axis of the shaft 26. The second ultrasonic transducer 30 is adapted for use in centering the probe 25 within the hole under inspection and, although preferred, it is not essential to effective operation of this embodiment of the present invention.

The second ultrasonic transducer 30 is oriented for radially outward direction of the axis of radiation of ultrasonic energy emanating therefrom. In operation, with the hole to be inspected filled with an acoustical coupling medium such as water, the longitudinal axis of the shaft 26 and the longitudinal axis of the hole to be inspected are mechanically aligned to be parallel to each other. The probe 25 is then positioned within the hole to be inspected such that the axis of radiation of ultrasonic energy emanating from the second ultrasonic transducer 30 intercepts the interior wall of the hole. The second ultrasonic transducer is then electrically stimulated to produce ultrasonic energy. A portion of the ultrasonic energy reflected at the interface of the water and the interior wall of the hole under inspection is received by the second ultrasonic transducer and converted to electrical signals. The amplitude of these electrical signals is monitored and the probe 25 is positioned to provide the maximum amplitude of these signals. Attainment of the maximum amplitude of such signals is indicative of the probe being centered within the hole to be inspected.

The first ultrasonic transducer 29 is mounted at a predetermined distance of offset "a" from the longitudinal axis of the shaft 26. This offset is analogous to the offset determined for the above described first embodiment of the ultrasonic probe 1 and is determined in accordance with the same expression (1). The above description relating the offset "a" to the desired angle of refraction "$\theta$" applies as well to the present embodiment. The first ultrasonic transducer 29 is oriented for directing the axis of radiation of ultrasonic energy emanating therefrom parallel to a line formed by the intersection of planes perpendicular to the longitudinal axes of the shaft 26 and the lateral extension 27.

Preferably, the first and second ultrasonic transducers 29 and 30, respectively, are conventional focused crystals having a common focal length and are mounted in a common plane which is perpendicular to the longitudinal axis of the shaft 26. As shown in FIG. 6, conventional lenses 31 and 32 are provided to protect the ultrasonic transducers 29 and 30, respectively, and to seal the recesses in which the ultrasonic transducers are mounted.

The focal length is chosen such that the focal point of the second ultrasonic transducer 30 is equal to the distance between the wall of the hole under inspection and the second ultrasonic transducer.

When the ultrasonic transducers are focused crystals having a common focal length, it is necessary to adjust the acoustical path length of the first ultrasonic transducer to maintain a constant acoustical path length from the first ultrasonic transducer to the wall of the hole under inspection in order to ensure that the focal point of the first ultrasonic transducer is located on the wall of the hole under inspection. As shown in FIG. 6, one manner of providing such adjustment is to include a laterally offset surface 33 on the lateral extension 27 of the shaft. With the arrangement of FIG. 6, the first ultrasonic transducer 29 is further oriented for directing the axis of radiation of ultrasonic energy opposite to the direction of the offset. The lateral offset distance "b" is determined by the following expression:

$$b = \left(\frac{D}{2}\right) - \sqrt{\left(\frac{D}{2}\right)^2 - a^2} \quad (2)$$

wherein: "b" is the offset distance; "D" is the diameter of the hole under inspection; and "a" is the offset determined by expression (1).

The probe 25 includes a groove or other suitable passage (partially shown) wherein electrical leads are run. Each ultrasonic transducer has at least one electrical lead attached to it which runs from the respective transducer to the electrical connector 28. Only one lead is needed for each transducer if the shaft is of an electrically conductive material and is used as a common electrical ground reference.

The present invention is generally applicable to ultrasonic inspection in various modes. For example, the invention may be employed in connection with surface wave inspection, longitudinal wave inspection, and shear wave inspection. Once the invention is conceived, it is well known in the art that each of these modes of inspection require that the offset inspection transducer be positioned in a predetermined manner in accordance with previously discussed expressions (1) and (2). Further, the present invention is not limited to applications involving the inspection of cylindrical recesses such as bolt holes and bore holes. Indeed, the present invention is generally applicable to the inspection of other recesses, such as egg-shaped, triangular, and other conventional recess configurations.

Although the preferred embodiments of the present invention have been described and illustrated, other configurations and modifications will become apparent from the foregoing to one skilled in the art. Accordingly, it is intended that the scope of this invention be limited only by the appended claims.

What I claim as new and desire to secure by Letters Patent of the United States is:

1. An ultrasonic probe for nondestructive detection of anomalies in the region of a generally cylindrical hole comprising:
   (a) an elongated shaft having a longitudinal axis;
   (b) a first ultrasonic transducer which is
      (i) mounted at a predetermined distance from the longitudinal axis on a lateral offset surface located on a lateral extension of the shaft, the lateral offset surface being
         (A) located at an outer end section of the lateral extension,
         (B) offset a distance determined by the expression $$b = \left(\frac{D}{2}\right) - \sqrt{\left(\frac{D}{2}\right)^2 - a^2}$$

wherein:
      b = offset distance
      D = diameter of hole under inspection
      a = the predetermined distance of (b)(i),
      (ii) oriented for directing the axis of radiation of ultrasonic energy emanating therefrom opposite to the direction of offset and in a plane perpendicular to the longitudinal axis of (a),
   (c) a second ultrasonic transducer which
      (i) has a common focal length as the first ultrasonic transducer,
      (ii) is mounted on the longitudinal axis of (a) and in a common plane with the first ultrasonic transducer, the plane being perpendicular to the longitudinal axis, and
      (iii) is oriented for directing radiation radially outwardly of the longitudinal axis of (a).

2. An ultrasonic probe for nondestructive detection of anomalies near a generally cylindrical hole in an object by subjecting said object to ultrasonic energy comprising:
   (a) an elongated shaft having a lateral cutout with a planar bottom parallel to the longitudinal axis of said shaft and an internal longitudinal passage along the length of said shaft;
   (b) an ultrasonic transducer mounted in said planar bottom at a predetermined distance from the longitudinal axis of said shaft wherein said predetermined distance is determined by the expression:

$$a = \left(\frac{D}{2}\right) \times \left(\frac{V1}{V2}\right) \times \sin\theta$$

wherein:
   a = predetermined distance
   D = diameter of hole under inspection
   V1 = longitudinal velocity of sound in water
   V2 = inspection mode velocity in object under inspection
   θ = desired ultrasonic refracted angle (c) and said transducer is oriented for directing the axis of radiation of ultrasonic energy emanating therefrom outwardly in a plane perpendicular to said longitudinal axis of said shaft; and
   (d) at least one electrical lead connected to said ultrasonic transducer and positioned within said passage.

3. An ultrasonic probe for nondestructive detection of anomalies near a generally cylindrical hole in an object by subjecting said object to ultrasonic energy comprising:
   (a) an elongated shaft having a lateral extension and a longitudinal groove along the length of said shaft;
   (b) a first ultrasonic transducer mounted on said shaft on the longitudinal axis thereof and oriented for radially outward direction of the axis of radiation of ultrasonic energy emanating therefrom;
   (c) said lateral extension having a laterally offset outer end section with the offset distance of said outer end section being determined by the expression:

$$b = \left(\frac{D}{2}\right) - \sqrt{\left(\frac{D}{2}\right)^2 - a^2}$$

wherein:
   b = offset distance
   D = diameter of hole under inspection
   a = the distance between the first transducer and the longitudinal axis in (b)

(d) a second ultrasonic transducer mounted on said lateral offset and oriented for directing the axis of radiation of ultrasonic energy emanating therefrom opposite to the direction of the offset and parallel to a line formed by the intersection of a pair of planes extending respectively perpendicular to the longitudinal axis of said shaft and lateral extension; and
   (e) wherein said first and second ultrasonic transducers are focused crystals having a common focal length and are mounted in a common plane extending perpendicular to the longitudinal axis of said shaft.

4. A method of ultrasonic inspection of a generally cylindrical hole comprising the steps of:
   (a) transmitting ultrasonic radiation from a first focused transducer to the wall through a medium acoustically coupling the first transducer with the wall and along an axis which is
      (i) parallel to a radius of the hole and
      (ii) offset a predetermined distance from the radius of (a)(i),
   (b) transmitting ultrasonic radiation from a second focused transducer to the wall along the radius of (a)(i) and through the medium of (a), the second focused transducer
      (i) being laterally offset a predetermined distance from the first focused transducer and
      (ii) having a focal length substantially identical to the focal length of the first focused transducer.

* * * * *